United States Patent
Mallinson

(10) Patent No.: US 10,515,485 B2
(45) Date of Patent: Dec. 24, 2019

(54) SCANNING DISPLAY SYSTEM IN HEAD-MOUNTED DISPLAY FOR VIRTUAL REALITY

(71) Applicant: Sony Interactive Entertainment Inc., Tokyo (JP)

(72) Inventor: Dominic S. Mallinson, Redwood City, CA (US)

(73) Assignee: Sony Interactive Entertainment Inc., Tokyo (JP)

( * ) Notice: Subject to any disclaimer, the term of this patent is extended or adjusted under 35 U.S.C. 154(b) by 0 days.

(21) Appl. No.: 15/813,950

(22) Filed: Nov. 15, 2017

(65) Prior Publication Data

US 2018/0082484 A1 Mar. 22, 2018

Related U.S. Application Data

(63) Continuation of application No. 14/627,406, filed on Feb. 20, 2015, now Pat. No. 9,824,498.

(Continued)

(51) Int. Cl.
| | |
|---|---|
| *G09G 5/10* | (2006.01) |
| *G06T 19/00* | (2011.01) |
| *G02B 27/01* | (2006.01) |
| *H04N 13/279* | (2018.01) |
| *H04N 13/344* | (2018.01) |

(Continued)

(52) U.S. Cl.
CPC ............ *G06T 19/006* (2013.01); *G02B 26/10* (2013.01); *G02B 27/017* (2013.01); *G02B 27/0172* (2013.01); *G06F 3/011* (2013.01); *G09G 3/003* (2013.01); *H04N 5/7491* (2013.01); *H04N 13/279* (2018.05); *H04N 13/344* (2018.05); *H04N 13/366* (2018.05); *H04N 13/398* (2018.05); *A61M 2230/63* (2013.01); *G02B 2027/011* (2013.01); *G02B 2027/014* (2013.01); *G02B 2027/0121* (2013.01); *G02B 2027/0138* (2013.01); *G02B 2027/0145* (2013.01); *G02B 2027/0178* (2013.01); *G02B 2027/0187* (2013.01); *G09G 2320/0261* (2013.01); *G09G 2340/16* (2013.01); *G09G 2350/00* (2013.01);

(58) Field of Classification Search
CPC ....... G06T 19/006; G06T 19/00; G06F 3/011; G06F 3/012; G02B 27/017
USPC ....................................................... 345/633
See application file for complete search history.

(56) References Cited

U.S. PATENT DOCUMENTS

| | | | |
|---|---|---|---|
| 7,312,766 B1 * | 12/2007 | Edwards .............. | G02B 27/017 248/115 |
| 2014/0267420 A1 * | 9/2014 | Schowengerdt ........ | G06F 3/012 345/633 |
| 2015/0002542 A1 * | 1/2015 | Chan ...................... | G06F 3/048 345/633 |

* cited by examiner

*Primary Examiner* — Gordon G Liu
(74) *Attorney, Agent, or Firm* — Penilla IP, APC

(57) ABSTRACT

Methods, systems, and computer programs are presented for the presentation of images in a head-mounted display (HMD). One HMD includes a screen, a processor, inertial sensors, a motion tracker module, and a display adjuster module. The motion tracker tracks motion of the HMD based on inertial data from the inertial sensors, and the display adjuster produces modified display data for an image frame to be scanned to the screen if the motion of the HMD is greater than a threshold amount of motion. The display data includes pixel values to be scanned to rows in sequential order, and the modified display data includes adjusted pixel values for pixels in a current pixel row of the image frame to compensate for the distance traveled by the HMD (Continued)

during a time elapsed between scanning a first pixel row of the image frame and scanning the current pixel row of the image frame.

20 Claims, 9 Drawing Sheets

Related U.S. Application Data

(60) Provisional application No. 62/098,228, filed on Dec. 30, 2014.

(51) Int. Cl.
*H04N 13/366* (2018.01)
*H04N 13/398* (2018.01)
*G06F 3/01* (2006.01)
*G09G 3/00* (2006.01)
*H04N 5/74* (2006.01)
*G02B 26/10* (2006.01)

(52) U.S. Cl.
CPC ..... *G09G 2354/00* (2013.01); *G09G 2360/18* (2013.01)

Head rotating left to right makes pixels displayed later in time to appear to the right Adjusted pixel may include a pixel value based on more than one pixels

SCANNING DISPLAY SYSTEM IN HEAD-MOUNTED DISPLAY FOR VIRTUAL REALITY

CLAIM OF PRIORITY

This application is a continuation of and claims priority to U.S. application Ser. No. 14/627,406, filed on Feb. 20, 2015, entitled "SCANNING DISPLAY SYSTEM IN HEAD-MOUNTED DISPLAY FOR VIRTUAL REALITY"; which claims priority from U.S. Provisional Patent Application No. 62/098,228, filed Dec. 30, 2014, and entitled "SCANNING DISPLAY SYSTEM IN HEAD-MOUNTED DISPLAY FOR VIRTUAL REALITY," all of which are herein incorporated by reference in their entireties.

BACKGROUND

1. Field of the Invention

The present embodiments relate to methods for improving presentation of a virtual reality in a Head Mounted Devices (HMD), and more particularly, methods, systems, and computer programs for manipulating display data when the head of the user wearing the HMD is in motion.

2. Description of the Related Art

Typically, an HMD is a portable device worn around the head, such that a display situated a short distance from the eyes provides images for user interaction. Sometimes HMDs provide a mixed real-life and virtual life environments, where the user is able to see images created by a computing device, as well as some real-live images. Other times HMDs provide immersive experiences that block the outside world to the user, while providing a virtual world on the HMD display.

However, there can be problems while the user views the real world or the virtual world through the display in the HMD because the computing capability of the HMD may not be adequate to refresh images on the display. This can cause motion sickness or vertigo to HMD users. This phenomenon is especially critical, when the user is moving the head and expects the static objects in the virtual reality to remain stationary and not being affected by the user motion.

What is needed is an HMD that manages the presentation of display data in the headmounted device in order to avoid having the motion of the user cause an undesirably effect on the perception of the virtual world.

It is in this context that embodiments arise.

SUMMARY

Methods, devices, systems, and computer programs are presented for managing the presentation of display data in a head-mounted display (HMD), and more specifically adjusting the presentation of the display based on the motion of the HMD. It should be appreciated that the present embodiments can be implemented in numerous ways, such as a method, an apparatus, a system, a device, or a computer program on a computer readable medium. Several embodiments are described below.

In one embodiment, a head-mounted display (HMD) includes a screen, a processor, inertial sensors operable to generate inertial data, a motion tracker module, and a display adjuster module. The motion tracker module is operable to be executed by the processor, and the motion tracker module is operable to track a motion of the head-mounted display (HMD) based on the inertial data. Further, the display adjuster module is operable to be executed by the processor, and the display adjuster module is operable to produce modified display data for an image frame to be scanned to the screen if the motion of the HMD is greater than a threshold amount of motion. The display data includes pixel values to be scanned to a plurality of pixel rows in sequential order (in another embodiment the pixel values are scanned to a plurality of pixel columns). The modified display data includes adjusted pixel values for pixels in a current pixel row of the image frame to compensate for a distance traveled by the HMD during a time elapsed between scanning a first pixel row of the image frame and scanning the current pixel row of the image frame, and the adjusted pixel values are pixel values of pixels located at an offset distance of the pixels in the current pixel row. The offset distance is based on the rotation of the HMD during the time elapsed, and the modified display data for the image frame is scanned to the screen to reduce distortion due to the motion of the HMD. In one embodiment, the adjustment of the pixel values is done at the pixel level, i.e., the granularity of the adjustment and re-sampling of pixels can be at the pixel level instead of at the scan-line level.

In another embodiment, a method is provided. The method includes operations for tracking motion of a head-mounted display (HMD) at the HMD, and for receiving, at the HMD, display data from a computing device for presentation of a virtual reality on a display of the HMD. The method further includes an operation for modifying the display data to produce modified display data for an image frame to be scanned to a screen of the HMD if the motion of the HMD is greater than a threshold amount of motion. The display data includes pixel values to be scanned to a plurality of pixel rows in sequential order, where the modified display data includes adjusted pixel values for pixels in a current pixel row of the image frame to compensate for a distance traveled by the HMD during a time elapsed between scanning a first pixel row of the image frame and scanning the current pixel row of the image frame. The adjusted pixel values are pixel values of pixels located at an offset distance of the pixels in the current pixel row, the offset distance being based on the distance traveled by the HMD during the time elapsed. The method further includes an operation for presenting the modified display data on the display of the HMD.

In yet another embodiment, a non-transitory computer-readable storage medium, storing a computer program, includes program instructions for program instructions for tracking motion of a head-mounted display (HMD) at the HMD, and program instructions for receiving, at the HMD, display data from a computing device for presentation of a virtual reality on a display of the HMD. The storage medium further includes program instructions for modifying the display data to produce modified display data for an image frame to be scanned to the screen if the motion of the HMD is greater than a threshold amount of motion, the display data including pixel values to be scanned to a plurality of pixel rows in sequential order. The modified display data includes adjusted pixel values for pixels in a current pixel row of the image frame to compensate for a distance traveled by the HMD during a time elapsed between scanning a first pixel row of the image frame and scanning the current pixel row of the image frame, where the adjusted pixel values are pixel values of pixels located at an offset distance of the pixels in the current pixel row, the offset distance being based on the distance traveled by the HMD during the time elapsed. The storage medium further includes program instructions for presenting the modified display data on the display of the HMD.

Other aspects will become apparent from the following detailed description, taken in conjunction with the accompanying drawings.

BRIEF DESCRIPTION OF THE DRAWINGS

The embodiments may best be understood by reference to the following description taken in conjunction with the accompanying drawings.

DETAILED DESCRIPTION

The following embodiments describe methods, devices, systems, and computer programs for managing the presentation of display data in a head-mounted display (HMD), and more specifically adjusting the presentation of the display based on the motion of the HMD.

It will be apparent, that the present embodiments may be practiced without some or all of these specific details. In other instances, well-known process operations have not been described in detail in order not to unnecessarily obscure the present embodiments.

Embodiments presented herein relate to a headmounted display (HMD) that has inertial sensors and receives display data from a computer system (e.g., a gaming console, a personal computer, a smartphone, a cloud gaming service, etc.). In some embodiments, the computer system communicates with the HMD over a network, which introduces a transit time for transferring the display data from the computer system to the HMD. In other embodiments, the HMD could be coupled to the computer system, such as a smart phone attached to the HMD itself, which also requires a transfer time for sending the display data to the HMD. The HMD adjusts the display data being scanned on the display of the HMD to compensate for the motion of the head of the user, in order to solve the problem of having elements in a virtual reality appeared to be distorted due to the motion of the HMD.

In one embodiment, the corrections are done at the pixel level (or based on groups of pixels) and in real-time, and each pixel correction is based on the motion of the user and the timing for displaying the pixel. There is a tight loop between the sensing system (e.g., inertial sensors) and the display system that presents the data on the display of the HMD.

Instead of having to send motion data from the HMD to the remote system that generates the virtual reality on the HMD, the HMD modifies the pixel data without having to rely on the cooperation from the remote system. The HMD has a closed loop between the display data and the inertial data that allows for fine pixel data correction at the HMD.

Figure 1:
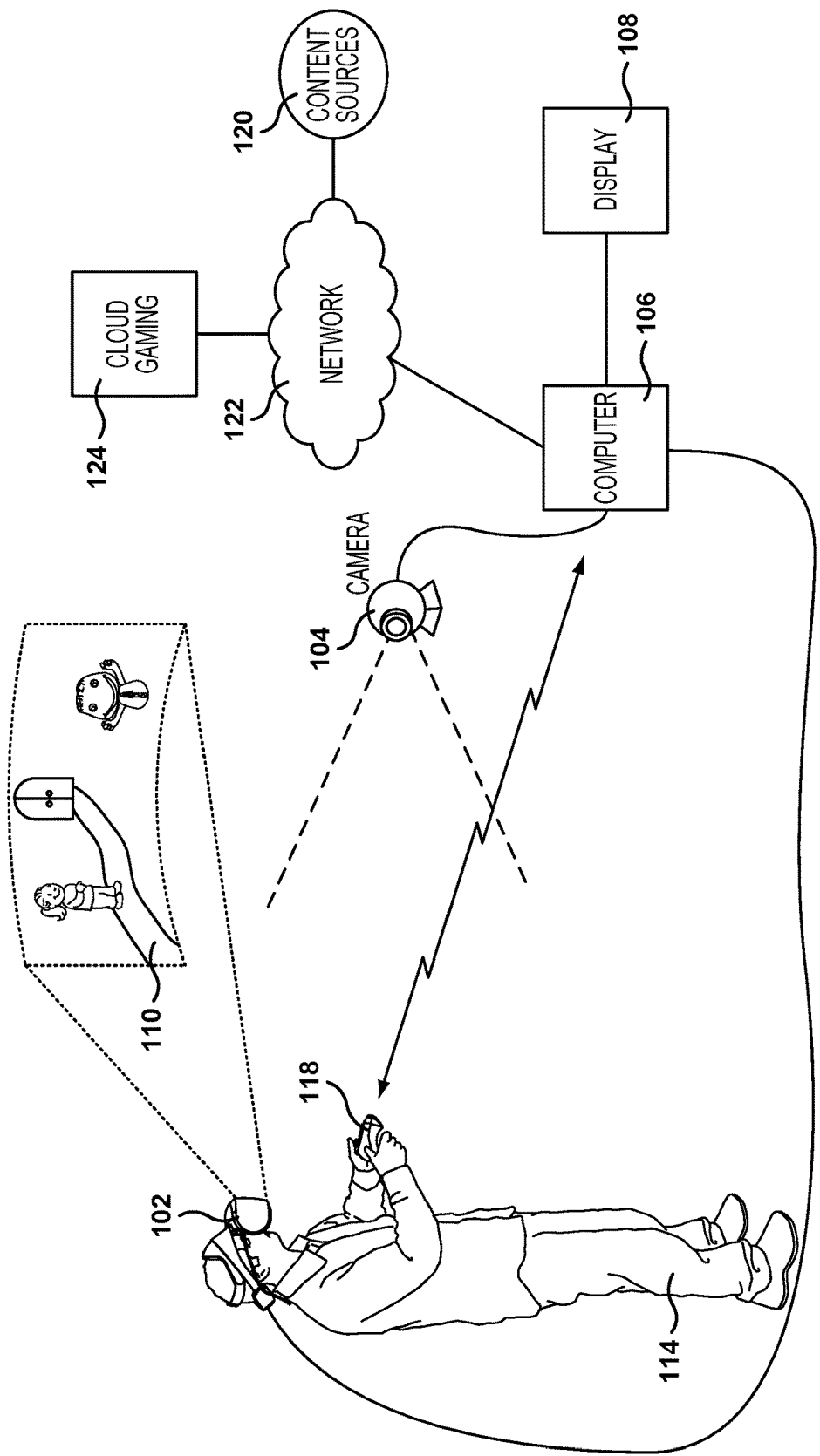
FIG. 1 illustrates a system for interactive gameplay of a video game, in accordance with an embodiment of the invention.

FIG. 1 illustrates a system for interactive gameplay of a video game, in accordance with an embodiment of the invention. A user 114 is shown wearing a head-mounted display (HMD) 102. The HMD 102 is worn in a manner similar to glasses, goggles, or a helmet, and is configured to display a video game or other content to the user 114. The HMD 102 is configured to provide an immersive experience to the user by virtue of its provision of display mechanisms (e.g., optics and display screens) in close proximity to the user's eyes and the format of the content delivered to the HMD. In one example, the HMD 102 can provide display regions to each of the user's eyes which occupy large portions or even the entirety of the field of view 110 of the user.

In one embodiment, the HMD 102 can be connected to a computer 106. The connection to computer 106 can be wired or wireless. The computer 106 can be any general or special purpose computer, including but not limited to, a gaming console, personal computer, laptop, tablet computer, mobile device, cellular phone, tablet, thin client, set-top box, media streaming device, etc. In some embodiments, the HMD 102 can connect directly to the internet, which may allow for cloud gaming without the need for a separate local computer. In one embodiment, the computer 106 can be configured to execute a video game (and other digital content), and output the video and audio from the video game for rendering by the HMD 102. The computer 106 is also referred to herein as a client system 106, which in one example is a video game console. The processing of game operations may be done on the computing device 106, on the HMD 102, or in both computing device 106 and HMD 102.

The computer may, in some embodiments, be a local or remote computer, and the computer may run emulation software. In a cloud gaming embodiment, the computer is remote and may be represented by a plurality of computing services that may be virtualized in data centers, wherein game systems/logic can be virtualized and distributed to user over a network.

The user 114 may operate a controller 118 to provide input for the video game. In one example, a camera 104 can be configured to capture image of the interactive environment in which the user 114 is located. These captured images can be analyzed to determine the location and movements of the user 114, the HMD 102, and the controller 118. In one embodiment, the controller 118 includes a light (or lights)

which can be tracked to determine its location and orientation. Additionally, as described in further detail below, the HMD 102 may include one or more lights which can be tracked as markers to determine the location and orientation of the HMD 102 in substantial real-time during game play. In one embodiment, the computing device 106 calculates a relative position between the HMD 102 and the game controller 116. The relative position is then used by the game to move a game object in synchronism with the HMD 102.

The camera 104 can include one or more microphones to capture sound from the interactive environment. Sound captured by a microphone array may be processed to identify the location of a sound source. Sound from an identified location can be selectively utilized or processed to the exclusion of other sounds not from the identified location. Furthermore, the camera 104 can be defined to include multiple image capture devices (e.g. stereoscopic pair of cameras), an IR camera, a depth camera, and combinations thereof.

In some embodiments, computer 106 can execute games locally on the processing hardware of the computer 106. The games or content can be obtained in any form, such as physical media form (e.g., digital discs, tapes, cards, thumb drives, solid state chips or cards, etc.) or by way of download from the Internet, via network 122. In another embodiment, the computer 106 functions as a client in communication over a network with a cloud gaming provider 124. The cloud gaming provider 124 may maintain and execute the video game being played by the user 114. The computer 106 transmits inputs from the HMD 102, the controller 118 and the camera 104, to the cloud gaming provider, which processes the inputs to affect the game state of the executing video game. The output from the executing video game, such as video data, audio data, and haptic feedback data, is transmitted to the computer 106. The computer 106 may further process the data before transmission or may directly transmit the data to the relevant devices. For example, video and audio streams are provided to the HMD 102, whereas a vibration feedback command is provided to the controller 118.

In one embodiment, the HMD 102, controller 118, and camera 104, may themselves be networked devices that connect to the network 122 to communicate with the cloud gaming provider 124. For example, the computer 106 may be a local network device, such as a router, that does not otherwise perform video game processing, but facilitates passage network traffic. The connections to the network by the HMD 102, controller 118, and camera 104 may be wired or wireless. In some embodiments, content executed on the HMD 102 or displayable on a display 108, can be obtained from any content source 120. Example content sources can include, for instance, internet websites that provide downloadable content and/or streaming content. In some examples, the content can include any type of multimedia content, such as movies, games, static/dynamic content, pictures, social media content, social media websites, etc.

A player 114 may be playing a game on the HMD 102, where such content is immersive 3D interactive content. The content on the HMD 102, while the player is playing, can be shared to a display 108. In one embodiment, the content shared to the display 108 can allow other users proximate to the player 114 or remote to watch along with the user's play. In still further embodiments, another player viewing the game play of player 114 on the display 108 may participate interactively with player 114. For example, a user viewing the game play on the display 108 may control characters in the game scene, provide feedback, provide social interaction, and/or provide comments (via text, via voice, via actions, via gestures, etc.,) which enables users that are not wearing the HMD 102 to socially interact with player 114, the game play, or content being rendered in the HMD 102.

It is noted that the embodiments illustrated in FIG. 1 are exemplary. Other embodiments may utilize different devices, a different number of devices, have more or less interaction between the different devices, use other ways of communication (e.g. ultrasonic), facilitate a multiplayer game with two users wearing respective HMD's play the same game, etc. The embodiments illustrated in FIG. 1 should therefore not be interpreted to be exclusive or limiting, but rather exemplary or illustrative.

Figure 2A:
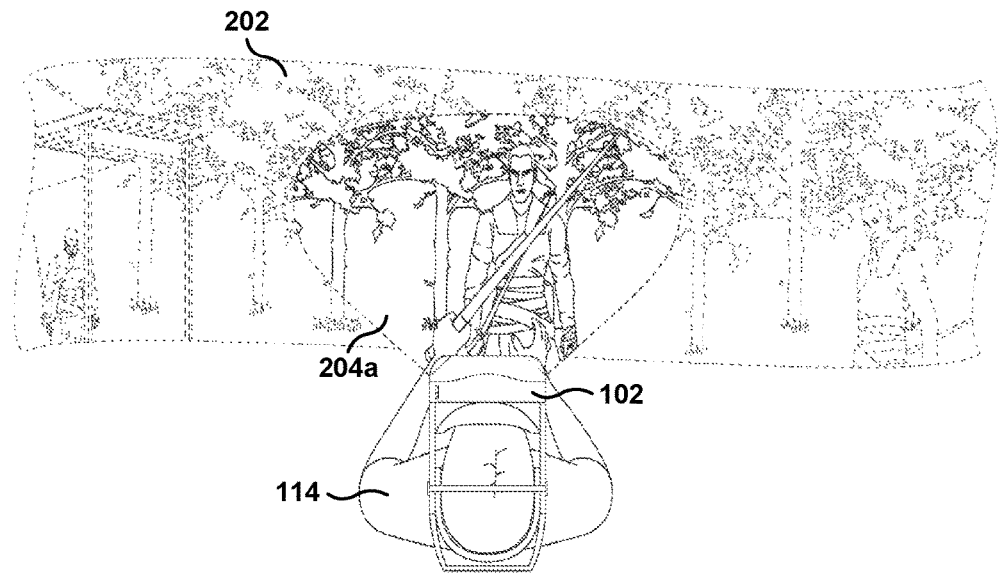
FIGS. 2A-2B illustrate the view of a player wearing a head-mounted display (HMD), according to one embodiment.
Figure 2B:
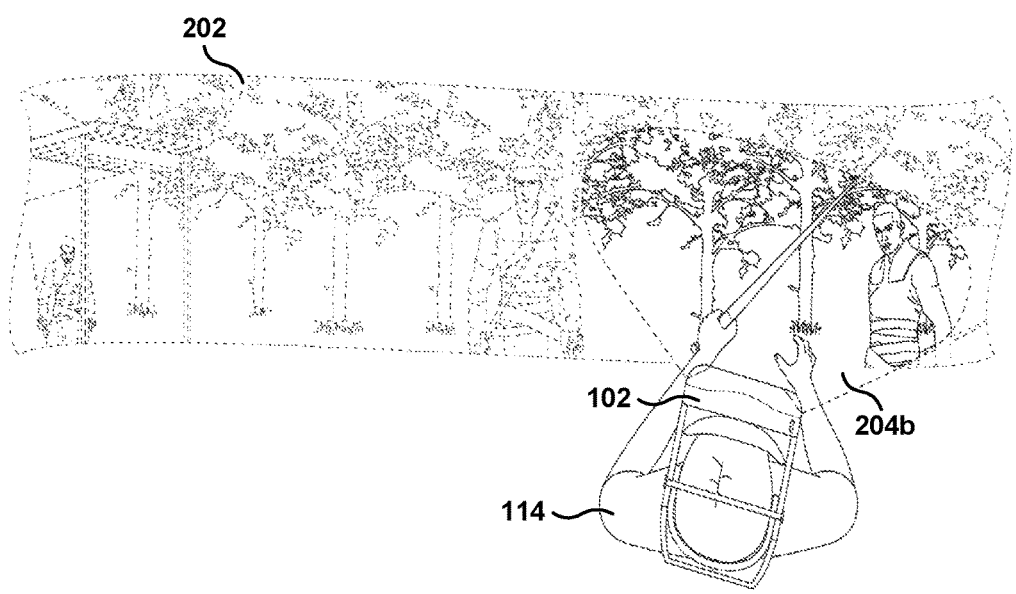

FIGS. 2A-2B illustrate the view of a player wearing a head-mounted display (HMD), according to one embodiment. In the embodiment of FIG. 2A, player 114 is viewing a virtual reality 202 through HMD 102. The virtual reality extends beyond the field of view 204*a* of the user, and as the user moves the head, the view of the virtual reality changes, as if the HMD were a camera pointing to the virtual reality. This provides an immersion feeling to the user within the virtual reality 202 because as the user moves her sight, the view of the virtual reality world changes accordingly.

FIG. 2B illustrates the changing of the field of view 204*b* of the user 114 when the user moves the HMD. The virtual reality 202 projected on the HMD 102 now corresponds to a different part of the virtual reality as shown in FIG. 2A.

The user may rotate the head producing horizontal changes to the virtual reality, or move the head up and down to generate vertical changes to the virtual reality, or any combination thereof. For example, in FIG. 2B the user has moved the HMD to the right and slightly downwards, causing the corresponding change in the view of the virtual reality.

In one embodiment, the virtual reality includes a virtual world with elements that are static and elements that may move within the game. The static elements include static objects in the scenery, such as houses, trees, permanent structures, the sun, mountains, etc. The elements that may move within the virtual reality includes virtual objects representing objects or people from the real world that would naturally move in the real world, such as game characters, people, animals, cars, etc.

A good virtual reality projection system gives the impression to the user that the static objects in the virtual reality remain always static as the user moves within the virtual reality. Sometimes, due to lack of processing resources, or if the user moves the HMD quickly, the projection of the virtual reality may be distorted, which may cause discomfort in the user and low satisfaction with the virtual reality projection.

Figure 3A:
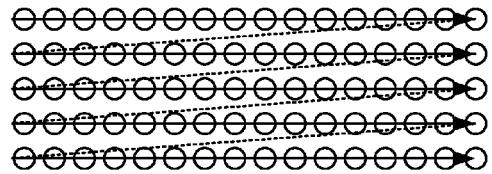
FIG. 3A illustrates the scanning of a display in an HMD, according to one embodiment.

FIG. 3A illustrates the scanning of a display in an HMD. In one embodiment, the display of the HMD is an organic light-emitting diode display (OLED) that includes a plurality of color pixels, where each pixel of display data is associated with three color LEDs. The principles presented herein can be utilized on any type of display that has raster data including pixels, such as a virtual retinal display, a cathode ray tube display (CRT), a light-emitting diode display (LED), an electroluminescent display (ELD), a plasma display panel (PDP), a thin-film transistor display (TFT), or a liquid crystal display (LCD).

A virtual retinal display (VRD), also known as a retinal scan display (RSD) or retinal projector (RP), is a display device that draws a raster display directly onto the retina of the eye. To create an image with the VRD, a photon source (or three sources in the case of a color display) is used to generate a coherent beam of light. The use of a coherent source (such as a laser diode) allows the system to draw a diffraction limited spot on the retina. The light beam is intensity modulated to match the intensity of the image being rendered. The modulation can be accomplished after the beam is generated.

The resulting modulated beam is then scanned to place each image point, or pixel, at the proper position on the retina. A variety of scan patterns are possible. The scanner could be used in a calligraphic (vector) mode, in which the lines that form the image are drawn directly, or in a raster mode, much like standard computer monitors or television. Use of the raster method of image scanning allows the VRD to be driven by standard video sources.

As seen in FIG. 3A, each circle represents a pixel, and to draw the raster, a horizontal scanner moves the beam to draw a row of pixels at a time. The scanner then moves the beam to the next line where another row of pixels is drawn. Typically, the scanning within a row is done from left to right.

For virtual reality (VR), it's desirable that the amount of time that the pixel is displayed is very short. For example, a pixel should be illuminated for 1 or 2 ms, but typical TVs may illuminate a pixel for about 16 ms, although other periods of time are also possible.

Figure 3B:
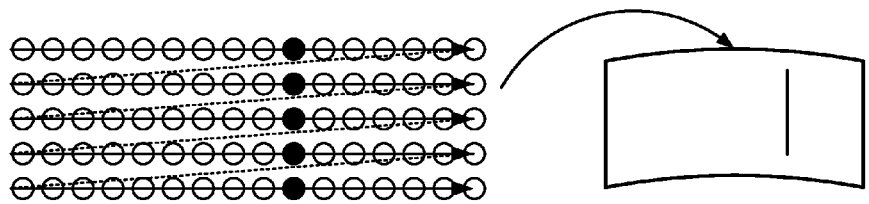
FIG. 3B illustrates the pixel representation by line presented on the display, according to one embodiment.

FIG. 3B illustrates the pixel representation by line presented on the display, according to one embodiment. If a black line is presented on the display, where the black line is one pixel wide, there will be a plurality of black pixels in the column within the raster that is associated with the line.

Since the lines are scanned to the display one at a time, there will be a period between displaying a pixel and displaying the pixel below in the next line. In some embodiments, the HMD receives display data from a remote computing device, and the HMD will start scanning pixels to the display even before the complete set of pixels for one complete raster is available in the HMD. In other words, the top left pixel of the display may be illuminated in the display before data for the bottom right pixel has been received.

In some embodiments, the remote computing device calculates the image at some instance in time and then sends the image (e.g., one scan of the display) to the HMD. Obviously, because it takes times to transmit and receive data, and because the data may be partitioned for transmission, the pixels arrive at the HMD at different points in time. Most critically, the pixels may arrive at many different points in time because the display may be using a serial interface. By the time the last pixel arrives, some period of time has elapsed since the first pixel arrived.

Figure 3C:
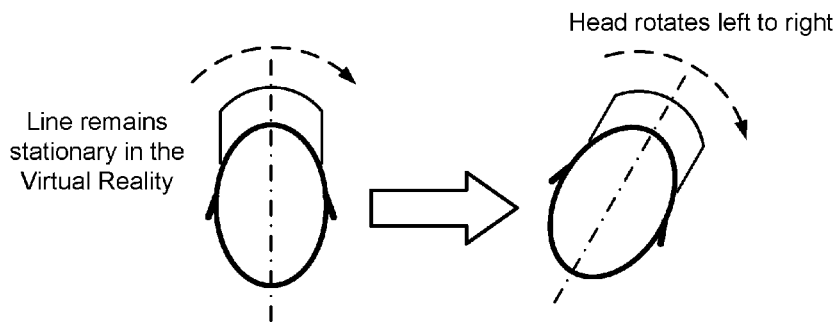
FIG. 3C illustrates the problem of keeping static objects stationary when the user rotates the head, according to one embodiment.

FIG. 3C illustrates the problem of keeping static objects stationary when the user rotates the head, according to one embodiment. As long as the HMD remains substantially stationary, the line appears to be a stationary in the virtual reality.

However, if the user rotates the head to the right at fast speed, the line might be distorted due to the associated change of the virtual reality due to the rotation of the head. This is due to the fact that not all pixels are displayed at the same time, and the pixels at the top of the line are displayed before the pixels below them.

Without being bound by theory, Applicant believes that the reason that images get distorted is because not all the pixels in a scan are displayed at the same time. For example, the first pixel on the raster is displayed at an initial time while the head of the user is in the first position, and a pixel on the next line is displayed at a later time when the head is in a different position. Of course, there could be other reasons for distortion on the display, but the embodiments presented herein provide methods for correcting pixel data based on the time elapsed between the presentation of pixels in the display and the motion of the head during the time elapsed.

Figure 3D:
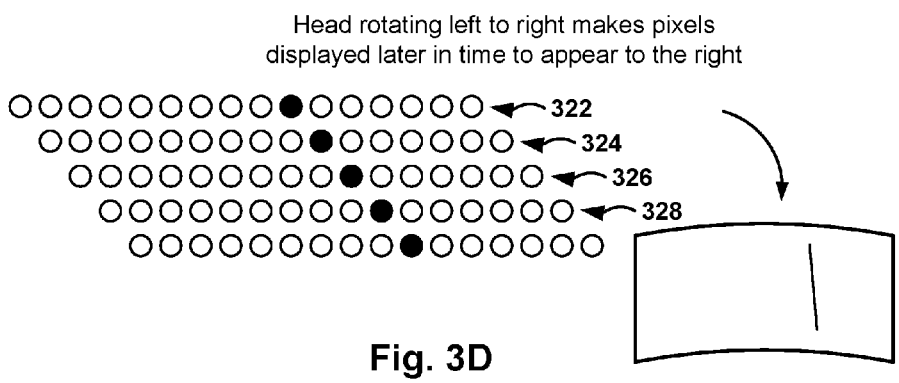
FIG. 3D illustrates the perception of a vertical line to the user when rotating the head, according to one embodiment.

FIG. 3D illustrates the perception of a vertical line to the user when rotating the head, according to one embodiment. In one scenario, a display is operating at 60 Hz, and displaying the complete raster takes about 17 ms. In a display with 720 lines, this means that each line takes about 0.02 ms to display. As the user moves the head, the HMD moves with the head, and if there is no correction, the pixels of the display move with the head. However, as the head moves, stationary objects should remain stationary. Assuming that the line is stationary in the background of the virtual reality, the line should be moving with reference to the field of vision of the display when the HMD is moving.

Therefore, the first pixel in line 322 is displayed at time t, the pixel in line 324 is displayed at time (t+0.02), the pixel in line 326 is displayed at time (t+0.04), etc. If the user is rotating the head to the right, the first pixel in 322 will be displayed when the head is in a first position, and the second pixel in 324 will be displayed when the head is at a second position. If the second pixel is presented right below the first pixel, the perception to the user is that the second pixel has moved to the right, because the motion of the head means that the second pixel would have to be presented below the first pixel in current time, but the first pixel "has moved" so the second pixel appears to have moved to the right. The process repeats for all the lines in the scan, and the result is that the vertical lines appear to be slightly off from vertical.

Figure 4A:
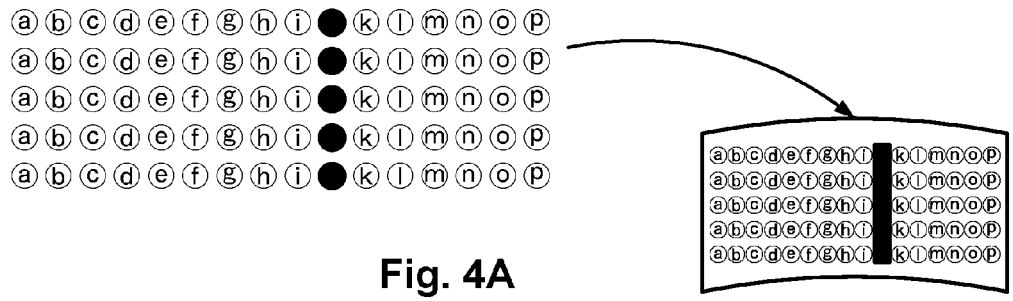
FIG. 4A illustrates the values for a plurality of pixels and the representation on the display of the HMD, according to one embodiment.

FIG. 4A illustrates the values for a plurality of pixels and the representation on the display of the HMD, according to one embodiment. As discussed above, each of the circles represents a pixel, and the pixels around the black line have been given an alphabetical value. The pixels for the black line are black.

Some implementations utilize what is called reprojection for the entire display basis. Given an entire image, when the user moves the head, the whole image is moved to compensate for the head motion. However, entire display reprojection doesn't solve the problem described hereinabove. Embodiments presented herein, correct the scanning data for the display to compensate for the motion of the HMD.

Figure 4B:
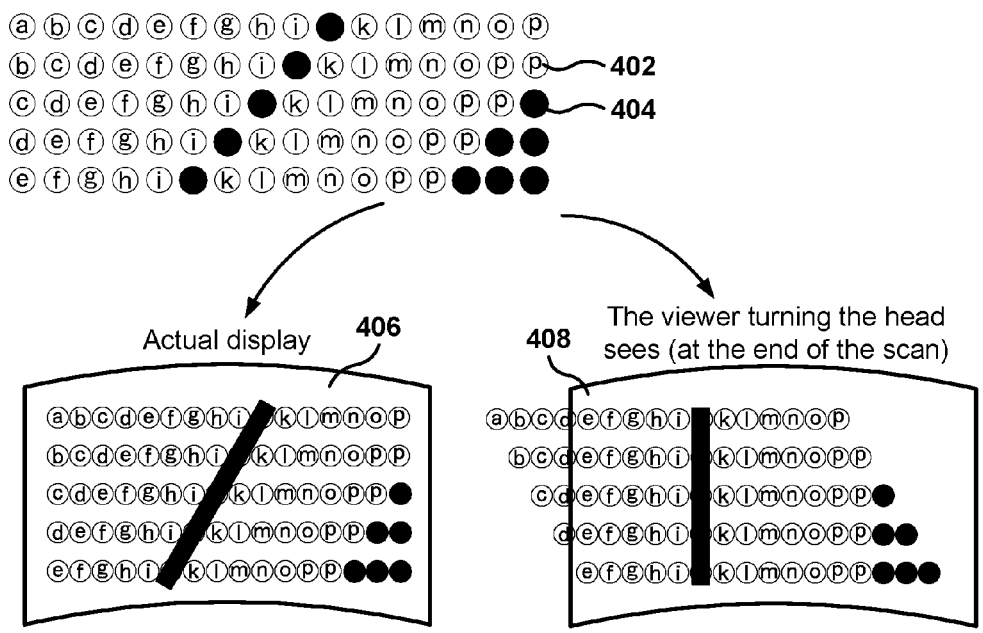
FIG. 4B illustrates the perception problem for the user when rotating the head, according to one embodiment.

FIG. 4B illustrates the perception problem for the user when rotating the head, according to one embodiment. The HMD includes inertial sensors to identify the motion of the HMD. The HMD does not have to wait for a remote computing device to track the motion of the HMD in order to calculate compensation adjustments. This allows the HMD to perform corrections on real time as the data comes in.

For ease of description, in this scenario it is assumed that the head is rotating in a way that when comparing a first pixel from a first line with a second pixel from the line below, the motion of the head is such that the displacement of the view is exactly one pixel between lines. This means that if the second pixel is placed one position to the left of the original position of the second pixel, then the second pixel would appear to be exactly below the first pixel because of the head rotation.

In the illustration of FIG. 4B, the pixels on the bottom line are therefore moved one place to the left. Of course, there is no pixel value for the last pixel on the right 402, so a value from neighboring pixel is given to pixel 402. In other cases, a black value is given to a pixel 404, which makes the edges of the display dark, and shouldn't be disturbing for the user in a wide field of view display.

From the calculation point of view, when time comes to display a pixel, the system determines what is the pixel value that should be used to eliminate distortion. In this example, the system takes a pixel value from a pixel to the right and uses that pixel value for the current pixel.

The result is that in the actual display 406 the line would be a tilted from vertical line (for a user that would not be moving the head), but for the viewer of the HMD display that is turning the head, the line appears to be vertical due to the adjustment of the pixel display data.

Figure 5:
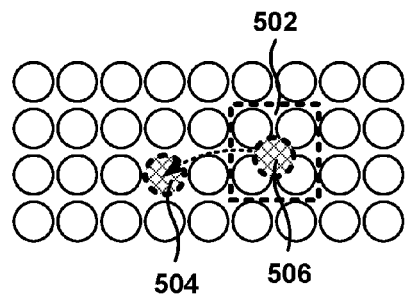
FIG. 5 depicts the method for calculating a pixel value during head motion, according to one embodiment.

FIG. 5 depicts the method for calculating a pixel value during head motion, according to one embodiment. In one embodiment, the display system in the HMD changes the pixel value before the pixel is displayed to compensate for the HMD motion.

In another embodiment, the scanning order is changed to accommodate for the motion. For example, if the head is rotating from left to right, the scanning of the display could be done by columns, instead of by rows. This mean that a first column of pixels would be scanned, from top to bottom or from bottom to top, and then the next column to the left (or to the right in another embodiment) is displayed next. Since the presentation of the pixels in the same column is almost simultaneously, the distortion effect described in FIG. 3D for a vertical line would not occur. However, this may cause a problem where the image does not shift to compensate for the motion of the head. The line would look vertical, but the background may appear to be shifting, instead of compensating for the rotation of the head. In this case, the same principles described below for a standard scanning display could be applied in a display that scans by columns, by shifting pixel values to the left or right, depending on the rotation of the head.

Returning to a standard scanning display, the embodiments described herein change pixel values before they are displayed, therefore, existing displays that scan by row can be utilized.

In one embodiment, the stream of display data arrives at the HMD and the display data is stored in the local raster scan memory. The display then emits those pixels based on the display data in the raster scan memory.

Before a pixel is presented, the system calculates how much the head has moved with reference to the beginning of the current scan, or with reference to other pixels in the display (e.g., the pixel situated right above). Based on the calculated motion, the value of the pixel is adjusted. In a way, it is the reverse of steering a beam. Because it is not possible to steer the beam, the system steers the raster scan memory.

In the exemplary embodiment of FIG. 5, the system calculates what pixel value to utilize for illuminating pixel 504. Due to the motion of the head since the beginning of the scan, the system determines that the pixel data compensated for the motion would be a virtual pixel 506 that is located between four pixels in area 502.

It is noted that pixels in FIG. 5 are represented as circles, but in other embodiments other shapes may be utilized to determine the area corresponding to a pixel, such as a square, rectangle, hexagon, etc.

Since virtual pixel 506 does not really exist, the actual pixel value attributed to pixel 504 is a function of the neighboring pixels in area 502. Of course, if the virtual pixel is situated substantially on top of an existing pixel, the value of that existing pixel would be utilized. If not, the value for pixel 504 is calculated as a weighted average of the pixels in area 502. For example, the average can provide equal weights to all the pixels, or the weights can be based on the overlap between the virtual pixel 506 and each of the pixels in area 502. In other embodiments, the pixel value may be also calculated based on other criteria, such as getting the pixel value from the closest actual pixel, or getting the average for an area that encompasses more than four pixels (e.g., 16 pixels), or using the leftmost topmost pixel in area 502, etc. In the embodiments where the value of another pixel in the raster is chosen, processing resources will be saved by not having to calculate weighted averages.

It may be the case that the data needed to make the adjustment and the pixel value has not arrived yet to the HMD. Of course, if the data is available, then that data is utilized. But if the data is not there yet, the HMD may utilize pixel data from the previous frame or based on the pixel data from two or more previous frames. The HMD caches the data from one or more previous frames in order to assist in the calculation of pixel values when needed.

When looking at the data from previous frames, in one embodiment, the data is taken from the value from the corresponding value of virtual pixel 506 in the previous frame. However, in another embodiment the calculation for the pixel adjustments includes calculating the motion of the HMD from the previous frame to the current frame, as well as the timing from the beginning of the scan. This way, a better pixel value is utilized that takes into account the motion of the HMD based on the age of the data utilized on the location of the pixel that is going to be illuminated or presented in the display.

In another embodiment, the mitigation plan for assigning pixel value when the data is not available refers to pixels that might be close to the edges of the screen and the data is not available in this frame or in previous frames. See for example, the pixels in the bottom lines of FIG. 4B. In one embodiment, the pixel values on the edges are given a black value, and in other embodiments the pixel are given a value-based on the available pixel values closest to the edge of the display.

In another embodiment, the display data is sent from the computing device at a faster rate than the refresh rate of the display. For example, if the display and HMD has a refresh rate of 120 Hz, the computer device may be sending display data at twice that rate, at 240 Hz. In this case, there is more data available for generating the pixel value predictions. It is possible that the HMD waits until more data arrives because there is a chance that better localization can be provided if a wait period is introduced.

Figure 6:
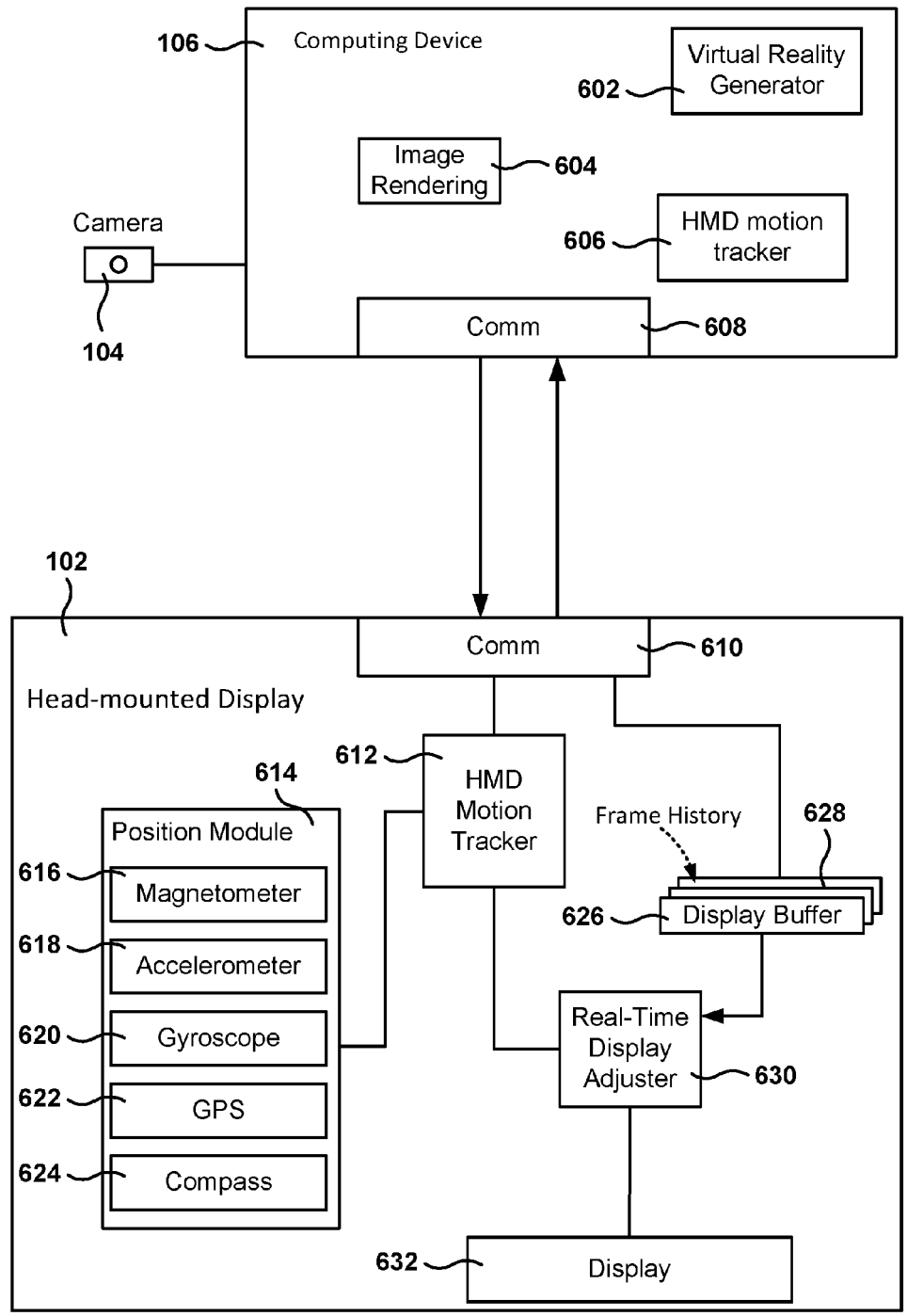
FIG. 6 illustrates an architecture for implementing embodiments presented herein.

FIG. 6 illustrates an architecture for implementing embodiments presented herein. In one embodiment, the computer device 106 includes a virtual reality generator 602, and image rendering module 604, an HMD motion tracker 606 and a communications module 608 for exchange of information with the HMD 102 or any other devices over a network.

In one embodiment, the HMD motion tracker 606 tracks the motion of the HMD utilizing input from camera 104 coupled to the computing device 106, and/or with data received from the inertial sensors in the HMD 102.

The virtual reality generator 602 is a module that maintains a view of a virtual reality world and calculates which part of the virtual world is visible at a given time to the viewer wearing the HMD. The virtual reality may be part of a game or some other interactive experience, such as virtual travel, virtual business, virtual communications, etc. In one embodiment, the virtual-reality includes the mixing of virtual elements with real-world elements, what is referred to as augmented reality. Also, the virtual-reality may include video images received from a remote computer device (e.g., teleconferencing, virtual presence).

The image rendering module 604 cooperates with virtual reality generator 602 to calculate the display data that will be displayed at a given point in time in the display of the HMD. Once the image rendering module 604 calculates the display data, the display data is transmitted to the HMD via the communications module 608. In one embodiment, the image rendering module 604 may perform image adjustments of the virtual-reality based on a prediction of the motion of the HMD, or based in the current trajectory of the HMD. When the image rendering module 604 performs motion prediction, the information is transmitted to the HMD 102, so the adjustment pixel values described above take into consideration the predictions performed by the image rendering module 604.

In one embodiment, the HMD 102 includes a position module 614, an HMD motion tracker module 612, a display 632, a real-time display adjuster module 630, a display buffer 626, and communications module 610.

The position module 614 calculates the position and motion of the HMD based on the data obtained by inertial sensors in the HMD. In one embodiment, the inertial sensors include one or more of a magnetometer 616, one or more accelerometers 618, one or more gyroscopes 620, a GPS module 622, or a compass 624.

The HMD motion tracker module 612 collects all the data from the inertial sensors and calculates the current motion of the HMD and makes predictions on the expected motion of the HMD based on historical motion data. The motion data calculated by the HMD motion tracker module 612 is utilized by the real-time display adjuster that calculates new pixel values for display data to be presented to the display 602, if the motion of the HMD is greater than a threshold amount of motion.

Display buffer 626 holds the display data received from computer device 106 received by communications module 610. In addition, the display buffer 626 includes one or more historic frames 628 of previously rendered frames. In one embodiment, the display buffer 626 is a circular buffer that includes enough amount of space in the circular buffer to accommodate two or more frames of data, but other embodiments may utilize other types of memory storage for holding data for a plurality of display frames.

The real-time display adjuster module 630 utilizes the data in the display buffer 626, and when necessary the historic data 628, together with the motion data received from the HMD motion tracker to adjust the pixel values before the pixels are presented to the display 602.

The advantage of having a real-time display adjuster module 630 is that there is a closed-loop in the HMD to adjust the display data based on motion data calculated at the HMD. There is no need to wait for the computer device to calculate the motion of the HMD, and then transmit the motion to the HMD, which might take too much time for acting on the display data in real-time, or substantially close to real-time.

More details about the components of the HMD 102 are provided below with reference to FIG. 8.

Figure 7:
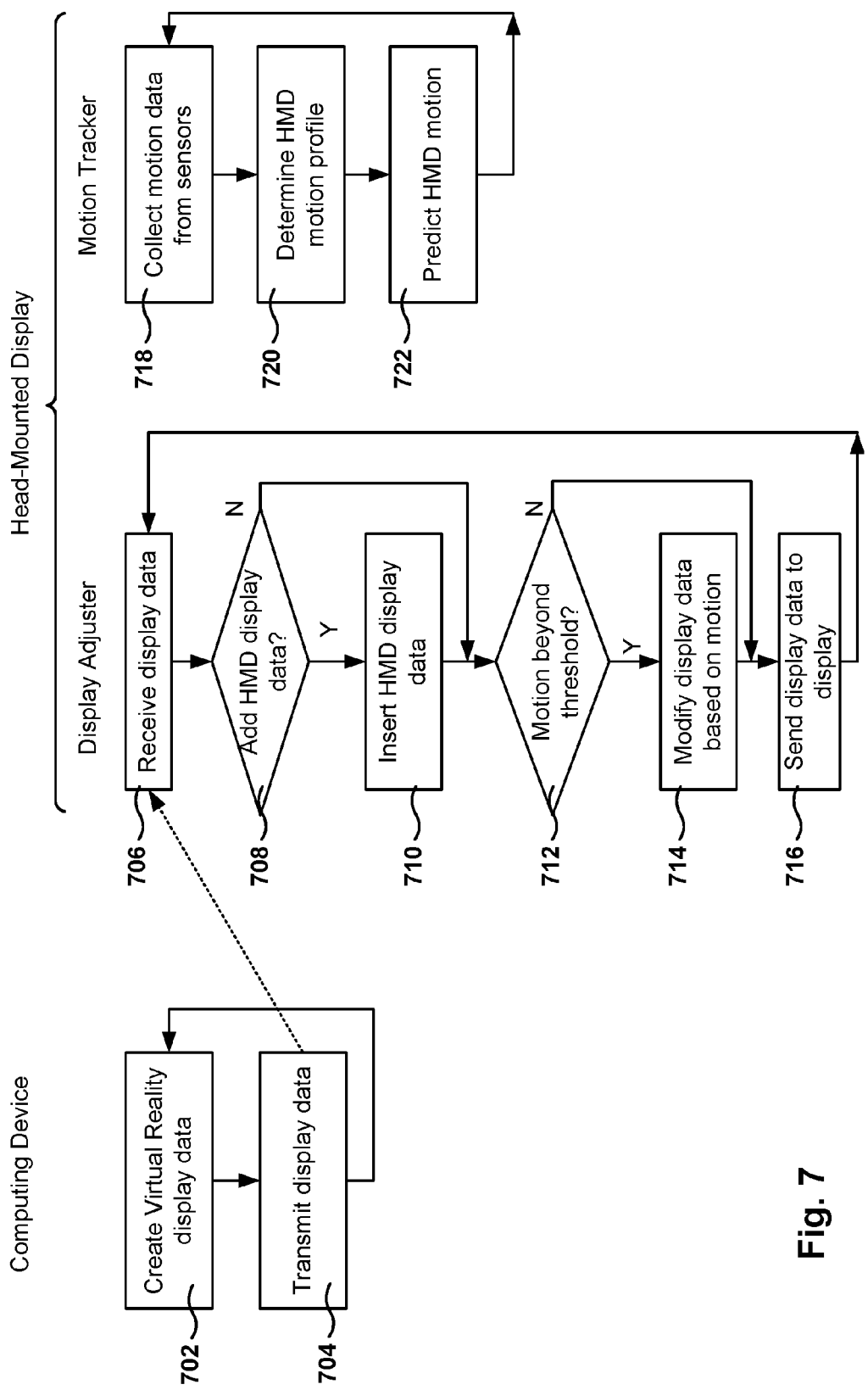
FIG. 7 is a flowchart for adjusting display data to compensate for HMD motion, according to one embodiment.

FIG. 7 is a flowchart for adjusting display data to compensate for HMD motion, according to one embodiment. While the various operations in this flowchart are presented and described sequentially, one of ordinary skill will appreciate that some or all of the operations may be executed in a different order, be combined or omitted, or be executed in parallel.

With reference to the computing device, in operation 702 the virtual reality display data is created at the computer device, and then the display data is transmitted from the computer device to the HMD in operation 704. From operation 704, the method flows back to operation 702.

With reference to the operations in display adjuster module of the HMD, in operation 706 the display data is received from the computer device. From operation 706, the method flows to operation 708 where a check is made to determine if the display data is to be modified with additional display data at the HMD. For example, the HMD may over impose a battery level indicator in the display, or some other information generated by the HMD and presented to the user.

If display data is to be added, the method flows to operation 710 where the corresponding HMD display data generated by the HMD is added to the display data received from the computer device. If no display data is to be added, the method flows to operation 712 where a check is made to determine if the HMD has moved beyond a threshold amount of movement. In one embodiment, the threshold amount of motion is the amount of motion that would cause distortion on the image presented on the display as perceived by the user wearing the HMD. In another embodiment, the threshold amount of motion is the amount of motion that would make pixel 506 (as described with reference to FIG. 5) closer to another pixel different from pixel 504, i.e., the adjusted pixel value for pixel 504 is closer to the value of a pixel different from pixel 504. In one embodiment, the pixel values are adjusted when the head rotates an amount that causes the angle traversed by the physical HMD, in the time between two successively scanned pixels, to be a significant proportion of the angular distance between pixels in the display system. The significant proportion value may be in the range from 10% to 100%, in some embodiments, although other values are also possible.

If the motion is greater than the threshold motion, the method flows to operation 714 where the display data is modified based on the motion. In one embodiment, the modification of the data is performed as described above with reference to FIG. 5.

From operation 714, the method flows to operation 716 where the display data is sent to the display for presentation. From operation 716, the method flows back to operation 706.

With reference to the motion tracker in the HMD, in operation 718 the motion tracker collects motion data from one or more sensors in the HMD. In one embodiment, motion data is also received from the computer device that is tracking the motion of the HMD (not shown in FIG. 7). In some embodiments, the sampling of the inertial data is significantly faster than the display frame rate, which allows for many opportunities to correct pixel data during the display frame time. For example, one inertial sensor may be sampled at 1,000 Hz, or even faster.

From operation 718, the method flows to operation 720 where the motion tracker determines the motion profile of the HMD. The motion profile refers to the motion experienced by the HMD from a predetermined amount of time to the current point in time when the calculation is performed. For example, the motion profile may take into account the motion of the HMD in the last few milliseconds. In some embodiments, the motion of the HMD is accounted for the most recent period of time in the range from 0.1 ms to about a second.

From operation 720, the method flows to operation 722 where the motion of the HMD is calculated and future motion is predicted. In one embodiment, the motion prediction includes a few milliseconds corresponding to about the scan rate of the HMD (e.g., about 1 ms), but other prediction periods may also be calculated.

In one embodiment, the most current motion of the HMD, when historical data is available, is given a higher weight when calculating the predicted motion of the HMD for the next few milliseconds. In one embodiment, a Kalman filter is used to combine the sensor data. From operation 722, the method flows back to operation 718.

Figure 8:
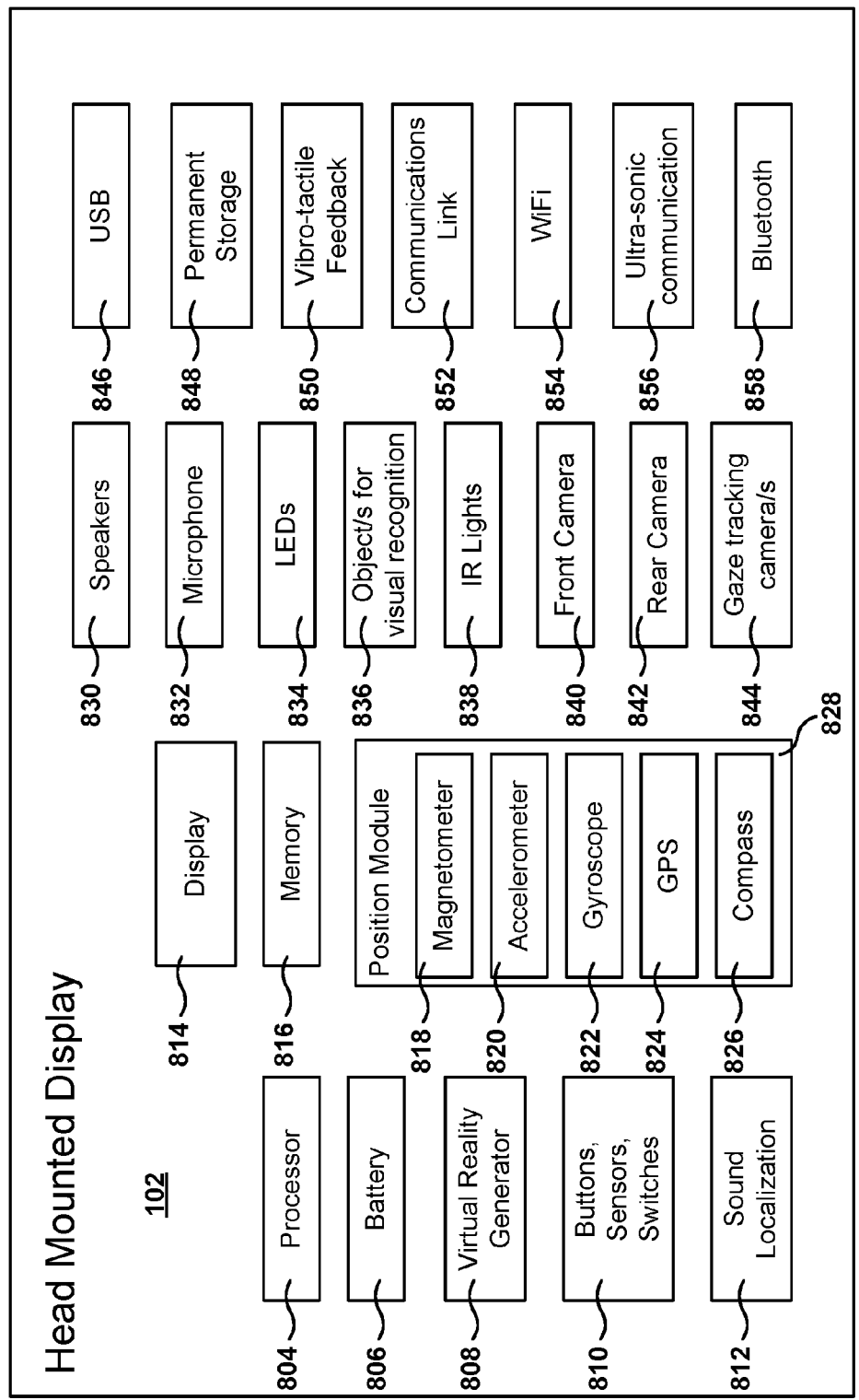
FIG. 8 illustrates the architecture of a device that may be used to implement embodiments.

FIG. 8 illustrates the architecture of a device that may be used to implement embodiments. The head-mounted display is a computing device and includes modules usually found on a computing device, such as a processor 804, memory 816 (RAM, ROM, etc.), one or more batteries 806 or other power sources, and permanent storage 848 (such as a hard disk).

The communication modules allow the HMD to exchange information with other portable devices, other computers, other HMD's, servers, etc. The communication modules include a Universal Serial Bus (USB) connector 846, a communications link 852 (such as Ethernet), ultrasonic communication 856, Bluetooth 858, and WiFi 854.

The user interface includes modules for input and output. The input modules include input buttons, sensors and switches 810, microphone 832, touch sensitive screen (not shown, that may be used to configure or initialize the HMD), front camera 840, rear camera 842, gaze tracking cameras 844. Other input/output devices, such as a keyboard or a mouse, can also be connected to the portable device via communications link, such as USB or Bluetooth.

The output modules include the display 814 for rendering images in front of the user's eyes. Some embodiments may include one display, two displays (one for each eye), micro projectors, or other display technologies. Other output modules include Light-Emitting Diodes (LED) 834 (which may also be used for visual tracking of the HMD), vibro-tactile feedback 850, speakers 830, and sound localization module 812, which performs sound localization for sounds to be delivered to speakers or headphones, providing a 3D sound simulation for objects rendered or displayed in the HMD to provide real-time 3D effect sounds. Other output devices, such as headphones, can also connect to the HMD via the communication modules.

The elements that may be included to facilitate motion tracking include LEDs 834, one or more objects for visual recognition 836, and infrared lights 838.

Information from different devices can be used by the Position Module 828 to calculate the position of the HMD. These modules include a magnetometer 818, an accelerometer 820, a gyroscope 822, a Global Positioning System (GPS) module 824, and a compass 826. Additionally, the Position Module can analyze sound or image data captured with the cameras and the microphone to calculate the position. Further yet, the Position Module can perform tests to determine the position of the portable device or the position of other devices in the vicinity, such as WiFi ping test or ultrasound tests.

A Virtual Reality Generator 808 creates the virtual or augmented reality, as previously described, using the position calculated by the Position Module. The virtual reality generator 808 may cooperate with other computing devices (e.g., game console, Internet server, etc.) to generate images for the display module 814. The remote devices may send screen updates or instructions for creating game objects on the screen.

The HMD 802 may be used for playing games, as discussed above, or for any other immersive experience. In one embodiment, the HMD is used for virtual inspection of a real world location, such as a hotel. This way, a user considering whether to go to a certain hotel may take a virtual tour with the HMD to check the hotel facilities and accommodations. In one embodiment, if the user likes the hotel, the user may also get reservations for the hotel during the virtual tour by accessing a menu that provides prices, choices, and available dates.

In another embodiment, the HMD may be used for shopping, such as by traveling with the HMD through a real store or a virtual store. As the user moves around the store, the user is able to check different items (e.g., articles for sale). If the user wants to purchase one or more items, a menu is provided for checking out the articles desired (e.g., virtual checkout).

In another embodiment, the virtual tour may be used for virtual tourism, allowing the HMD-wearing user to travel different locations around the world (e.g., the wall of China, the Golden Gate Bridge, the Eiffel Tower, etc.). An option may be provided to allow the user to do travel reservations to visit the desired location.

In one embodiment, the HMD is used for education. Students may access virtual lessons immersed in a virtual reality, or students may access class materials, in a classroom setting, using the HMD. For example, our students can travel through a virtual museum with a teacher, which provides description about the different pieces of art. In one embodiment, the view of the HMD is set by the teacher and the student's travel the virtual world sharing the same images as the teacher. This way, students may not wonder and visit other areas of the museum while the teacher is given a lecture.

In one embodiment, the rendering engine for the virtual reality generator utilizes forward prediction for the motions of the user, predicting which parts of the virtual world will the user visit. For example, if the user starts turning the head to the right, the rendering engine will start generating data to the right of the current view assuming that the user will continue turning to the right. Additionally, the rendering engine may provide higher resolution to the images on the right that the images on the left, because the user is turning her attention towards the right.

In one embodiment, an Application Programming Interface (API) is provided for developers to access the functionality of the HMD. The API may be provided for programs to be executed on the HMD, as well as for remote calls to access functionality within the HMD. In addition, the API may provide interfaces for accessing another device that is associated with the HMD, such as a game console in communication with the HMD, or any other devices interfacing with the HMD (e.g., a camera connected to the game console that tracks the movements of the user wearing the HMD). In one embodiment, a Software Development Kit (SDK) is provided to assist developers in creating applications that exploit the functionality of the API.

It should be appreciated that the embodiment illustrated in FIG. 8 is an exemplary implementation of a portable device. Other embodiments may utilize different modules, a subset of the modules, or assign related tasks to different modules. Additionally, the elements of the HMD may have different sizes, with some HMDs having miniaturized components to reduce a size of the HMD. In one embodiment, the HMD may look like a pair of glasses, where the virtual or augmented worlds are presented on the glass of the glasses or projected onto the retina of the user wearing the HMD.

The embodiment illustrated in FIG. 8 should therefore not be interpreted to be exclusive or limiting, but rather exemplary or illustrative.

Figure 9:
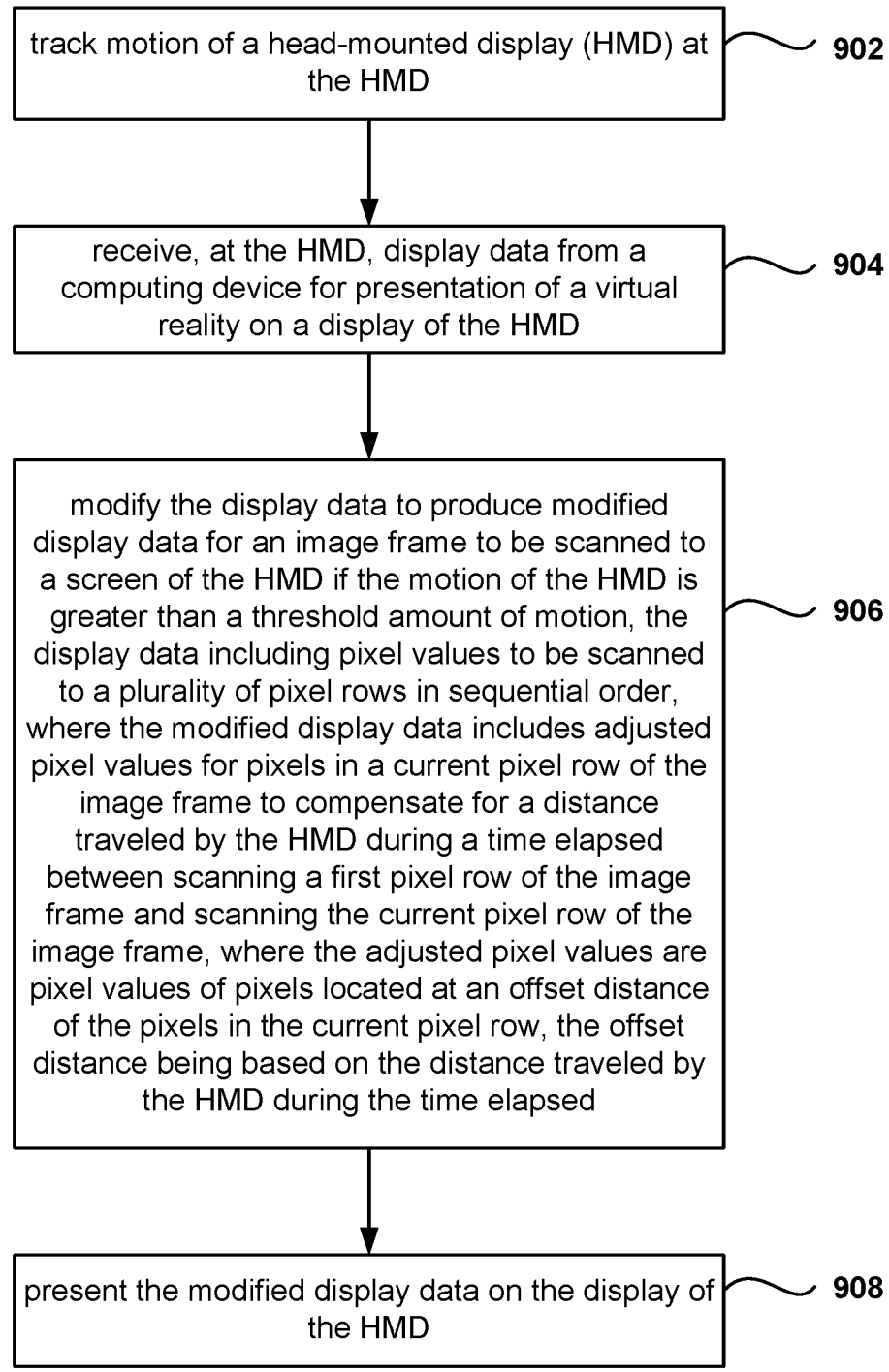
FIG. 9 is a flowchart for modifying the display data at an HMD utilizing inertial data from sensors in the HMD, according to one embodiment.

FIG. 9 is a flowchart for modifying the display data at an HMD utilizing inertial data from sensors in the HMD, according to one embodiment. While the various operations in this flowchart are presented and described sequentially, one of ordinary skill will appreciate that some or all of the operations may be executed in a different order, be combined or omitted, or be executed in parallel.

In operation 902, the motion of a head-mounted display (HMD) is tracked at the HMD. From operation 904, the method flows to operation 906 where display data is received from a computing device for presentation of a virtual reality on a display of the HMD.

From operation 906, the method flows to operation 908 where the display data is modified to produce modified display data for an image frame to be scanned to a screen of the HMD if the motion of the HMD is greater than a threshold amount of motion. The display data includes pixel values to be scanned to a plurality of pixel rows in sequential order, and the modified display data includes adjusted pixel values for pixels in a current pixel row of the image frame to compensate for a distance traveled by the HMD during a time elapsed between scanning a first pixel row of the image frame and scanning the current pixel row of the image frame.

The adjusted pixel values are pixel values of pixels located at an offset distance of the pixels in the current pixel row, the offset distance being based on the distance traveled by the HMD during the time elapsed. From operation 906, the method flows to operation 908 where the modified display data is presented on the display of the HMD.

Figure 10:
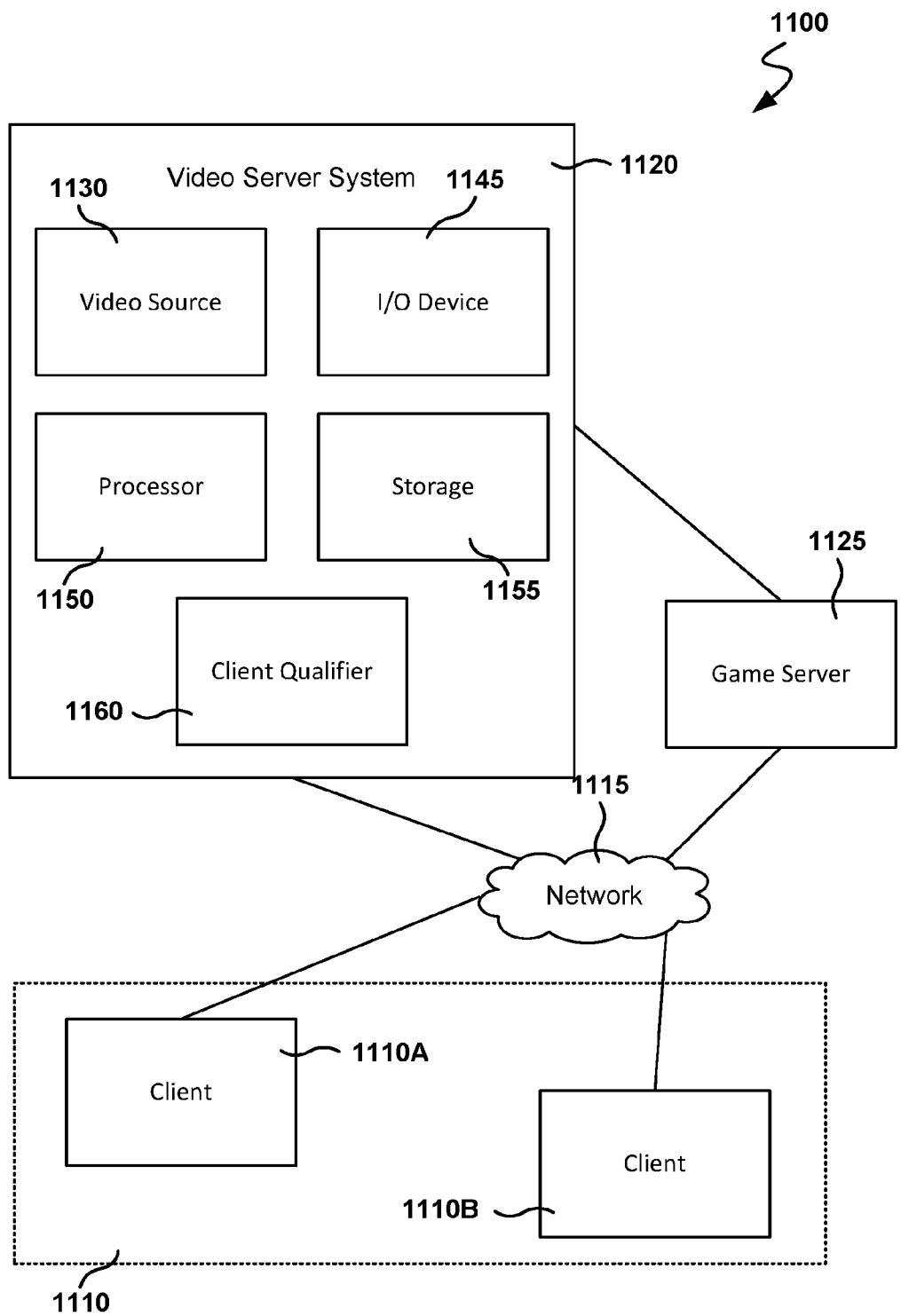
FIG. 10 is a block diagram of a game system, according to various embodiments.

FIG. 10 is a block diagram of a Game System 1100, according to various embodiments. Game System 1100 is configured to provide a video stream to one or more Clients 1110 via a Network 1115. Game System 1100 typically includes a Video Server System 1120 and an optional game server 1125. Video Server System 1120 is configured to provide the video stream to the one or more Clients 1110 with a minimal quality of service. For example, Video Server System 1120 may receive a game command that changes the state of or a point of view within a video game, and provide Clients 1110 with an updated video stream reflecting this change in state with minimal lag time. The Video Server System 1120 may be configured to provide the video stream in a wide variety of alternative video formats.

Clients 1110, referred to herein individually as 1110A., 1110B., etc., may include head mounted displays, terminals, personal computers, game consoles, tablet computers, telephones, set top boxes, kiosks, wireless devices, digital pads, stand-alone devices, handheld game playing devices, and/or the like. Typically, Clients 1110 are configured to receive encoded video streams, decode the video streams, and present the resulting video to a user, e.g., a player of a game. The processes of receiving encoded video streams and/or decoding the video streams typically includes storing individual video frames in a receive buffer of the client. The video streams may be presented to the user on a display integral to Client 1110 or on a separate device such as a monitor or television. Clients 1110 are optionally configured to support more than one game player. For example, a game console may be configured to support two, three, four or more simultaneous players. Each of these players may receive a separate video stream, or a single video stream may include regions of a frame generated specifically for each player, e.g., generated based on each player's point of view. Clients 1110 are optionally geographically dispersed. The number of clients included in Game System 1100 may vary widely from one or two to thousands, tens of thousands, or more. As used herein, the term "game player" is used to refer to a person that plays a game and the term "game playing device" is used to refer to a device used to play a game. In some embodiments, the game playing device may refer to a plurality of computing devices that cooperate to deliver a game experience to the user. For example, a game console and an HMD may cooperate with the video server system 1120 to deliver a game viewed through the HMD. In one embodiment, the game console receives the video stream from the video server system 1120, and the game console forwards the video stream, or updates to the video stream, to the HMD for rendering.

Clients 1110 are configured to receive video streams via Network 1115. Network 1115 may be any type of communication network including, a telephone network, the Internet, wireless networks, powerline networks, local area networks, wide area networks, private networks, and/or the like. In typical embodiments, the video streams are communicated via standard protocols, such as TCP/IP or UDP/IP. Alternatively, the video streams are communicated via proprietary standards.

A typical example of Clients 1110 is a personal computer comprising a processor, non-volatile memory, a display, decoding logic, network communication capabilities, and input devices. The decoding logic may include hardware, firmware, and/or software stored on a computer readable medium. Systems for decoding (and encoding) video streams are well known in the art and vary depending on the particular encoding scheme used.

Clients 1110 may, but are not required to, further include systems configured for modifying received video. For example, a client may be configured to perform further rendering, to overlay one video image on another video image, to crop a video image, and/or the like. For example, Clients 1110 may be configured to receive various types of video frames, such as I-frames, P-frames and B-frames, and to process these frames into images for display to a user. In some embodiments, a member of Clients 1110 is configured to perform further rendering, shading, conversion to 3-D, optical distortion processing for HMD optics, or like operations on the video stream. A member of Clients 1110 is optionally configured to receive more than one audio or video stream. Input devices of Clients 1110 may include, for example, a one-hand game controller, a two-hand game controller, a gesture recognition system, a gaze recognition system, a voice recognition system, a keyboard, a joystick, a pointing device, a force feedback device, a motion and/or location sensing device, a mouse, a touch screen, a neural interface, a camera, input devices yet to be developed, and/or the like.

The video stream (and optionally audio stream) received by Clients 1110 is generated and provided by Video Server System 1120. As is described further elsewhere herein, this video stream includes video frames (and the audio stream includes audio frames). The video frames are configured (e.g., they include pixel information in an appropriate data structure) to contribute meaningfully to the images displayed to the user. As used herein, the term "video frames" is used to refer to frames including predominantly information that is configured to contribute to, e.g. to effect, the images shown to the user. Most of the teachings herein with regard to "video frames" can also be applied to "audio frames."

Clients 1110 are typically configured to receive inputs from a user. These inputs may include game commands configured to change the state of the video game or otherwise affect game play. The game commands can be received using input devices and/or may be automatically generated by computing instructions executing on Clients 1110. The received game commands are communicated from Clients 1110 via Network 1115 to Video Server System 1120 and/or Game Server 1125. For example, in some embodiments, the game commands are communicated to Game Server 1125 via Video Server System 1120. In some embodiments, separate copies of the game commands are communicated from Clients 1110 to Game Server 1125 and Video Server System 1120. The communication of game commands is optionally dependent on the identity of the command. Game commands are optionally communicated from Client 1110A through a different route or communication channel that that used to provide audio or video streams to Client 1110A.

Game Server 1125 is optionally operated by a different entity than Video Server System 1120. For example, Game Server 1125 may be operated by the publisher of a multiplayer game. In this example, Video Server System 1120 is optionally viewed as a client by Game Server 1125 and optionally configured to appear from the point of view of Game Server 1125 to be a prior art client executing a prior art game engine. Communication between Video Server System 1120 and Game Server 1125 optionally occurs via Network 1115. As such, Game Server 1125 can be a prior art multiplayer game server that sends game state information to multiple clients, one of which is game server system 1120. Video Server System 1120 may be configured to communicate with multiple instances of Game Server 1125 at the same time. For example, Video Server System 1120 can be configured to provide a plurality of different video games to different users. Each of these different video games may be supported by a different Game Server 1125 and/or published by different entities. In some embodiments, several geographically distributed instances of Video Server System 1120 are configured to provide game video to a plurality of different users. Each of these instances of Video Server System 1120 may be in communication with the same instance of Game Server 1125. Communication between Video Server System 1120 and one or more Game Server 1125 optionally occurs via a dedicated communication channel. For example, Video Server System 1120 may be connected to Game Server 1125 via a high bandwidth channel that is dedicated to communication between these two systems.

Video Server System 1120 comprises at least a Video Source 1130, an I/O Device 1145, a Processor 1150, and non-transitory Storage 1155. Video Server System 1120 may include one computing device or be distributed among a plurality of computing devices. These computing devices are optionally connected via a communications system such as a local area network.

Video Source 1130 is configured to provide a video stream, e.g., streaming video or a series of video frames that form a moving picture. In some embodiments, Video Source 1130 includes a video game engine and rendering logic. The video game engine is configured to receive game commands from a player and to maintain a copy of the state of the video game based on the received commands. This game state includes the position of objects in a game environment, as well as typically a point of view. The game state may also include properties, images, colors and/or textures of objects. The game state is typically maintained based on game rules, as well as game commands such as move, turn, attack, set focus to, interact, use, and/or the like. Part of the game engine is optionally disposed within Game Server 1125. Game Server 1125 may maintain a copy of the state of the game based on game commands received from multiple players using geographically disperse clients. In these cases, the game state is provided by Game Server 1125 to Video Source 1130, wherein a copy of the game state is stored and rendering is performed. Game Server 1125 may receive game commands directly from Clients 1110 via Network 1115, and/or may receive game commands via Video Server System 1120.

Video Source 1130 typically includes rendering logic, e.g., hardware, firmware, and/or software stored on a computer readable medium such as Storage 1155. This rendering logic is configured to create video frames of the video stream based on the game state. All or part of the rendering logic is optionally disposed within a graphics processing unit (GPU). Rendering logic typically includes processing stages configured for determining the three-dimensional spatial relationships between objects and/or for applying appropriate textures, etc., based on the game state and viewpoint. The rendering logic produces raw video that is then usually encoded prior to communication to Clients 1110. For example, the raw video may be encoded according to an Adobe Flash® standard, .wav, H.264, H.263, On2, VP6, VC-1, WMA, Huffyuv, Lagarith, MPG-x. Xvid. FFmpeg, x264, VP6-8, realvideo, mp3, or the like. The encoding process produces a video stream that is optionally packaged for delivery to a decoder on a remote device. The video stream is characterized by a frame size and a frame rate. Typical frame sizes include 800×600, 1280×720 (e.g., 720p), 1024×768, although any other frame sizes may be used. The frame rate is the number of video frames per second. A video stream may include different types of video frames. For example, the H.264 standard includes a "P" frame and a "I" frame. I-frames include information to refresh all macro blocks/pixels on a display device, while P-frames include information to refresh a subset thereof. P-frames are typically smaller in data size than are I-frames. As used herein the term "frame size" is meant to refer to a number of pixels within a frame. The term "frame data size" is used to refer to a number of bytes required to store the frame.

In alternative embodiments Video Source 1130 includes a video recording device such as a camera. This camera may be used to generate delayed or live video that can be included in the video stream of a computer game. The resulting video stream, optionally includes both rendered images and images recorded using a still or video camera. Video Source 1130 may also include storage devices configured to store previously recorded video to be included in a video stream. Video Source 1130 may also include motion or positioning sensing devices configured to detect motion or position of an object, e.g., person, and logic configured to determine a game state or produce video-based on the detected motion and/or position.

Video Source 1130 is optionally configured to provide overlays configured to be placed on other video. For example, these overlays may include a command interface, log in instructions, messages to a game player, images of other game players, video feeds of other game players (e.g., webcam video). In embodiments of Client 1110A including a touch screen interface or a gaze detection interface, the overlay may include a virtual keyboard, joystick, touch pad, and/or the like. In one example of an overlay a player's voice is overlaid on an audio stream. Video Source 1130 optionally further includes one or more audio sources.

In embodiments wherein Video Server System 1120 is configured to maintain the game state based on input from more than one player, each player may have a different point of view comprising a position and direction of view. Video Source 1130 is optionally configured to provide a separate video stream for each player based on their point of view. Further, Video Source 1130 may be configured to provide a different frame size, frame data size, and/or encoding to each of Client 1110. Video Source 1130 is optionally configured to provide 3-D video.

I/O Device 1145 is configured for Video Server System 1120 to send and/or receive information such as video, commands, requests for information, a game state, gaze information, device motion, device location, user motion, client identities, player identities, game commands, security information, audio, and/or the like. I/O Device 1145 typically includes communication hardware such as a network card or modem. I/O Device 1145 is configured to communicate with Game Server 1125, Network 1115, and/or Clients 1110.

Processor 1150 is configured to execute logic, e.g. software, included within the various components of Video Server System 1120 discussed herein. For example, Processor 1150 may be programmed with software instructions in order to perform the functions of Video Source 1130, Game Server 1125, and/or a Client Qualifier 1160. Video Server System 1120 optionally includes more than one instance of Processor 1150. Processor 1150 may also be programmed with software instructions in order to execute commands received by Video Server System 1120, or to coordinate the operation of the various elements of Game System 1100 discussed herein. Processor 1150 may include one or more hardware device. Processor 1150 is an electronic processor.

Storage 1155 includes non-transitory analog and/or digital storage devices. For example, Storage 1155 may include an analog storage device configured to store video frames. Storage 1155 may include a computer readable digital storage, e.g. a hard drive, an optical drive, or solid state storage. Storage 1115 is configured (e.g. by way of an appropriate data structure or file system) to store video frames, artificial frames, a video stream including both video frames and artificial frames, audio frame, an audio stream, and/or the like. Storage 1155 is optionally distributed among a plurality of devices. In some embodiments, Storage 1155 is configured to store the software components of Video Source 1130 discussed elsewhere herein. These components may be stored in a format ready to be provisioned when needed.

Video Server System 1120 optionally further comprises Client Qualifier 1160. Client Qualifier 1160 is configured for remotely determining the capabilities of a client, such as Clients 1110A or 1110B. These capabilities can include both the capabilities of Client 1110A itself as well as the capabilities of one or more communication channels between Client 1110A and Video Server System 1120. For example, Client Qualifier 1160 may be configured to test a communication channel through Network 1115.

Client Qualifier 1160 can determine (e.g., discover) the capabilities of Client 1110A manually or automatically. Manual determination includes communicating with a user of Client 1110A and asking the user to provide capabilities. For example, in some embodiments, Client Qualifier 1160 is configured to display images, text, and/or the like within a browser of Client 1110A. In one embodiment, Client 1110A is an HMD that includes a browser. In another embodiment, client 1110A is a game console having a browser, which may be displayed on the HMD. The displayed objects request that the user enter information such as operating system, processor, video decoder type, type of network connection, display resolution, etc. of Client 1110A. The information entered by the user is communicated back to Client Qualifier 1160.

Automatic determination may occur, for example, by execution of an agent on Client 1110A and/or by sending test video to Client 1110A. The agent may comprise computing instructions, such as java script, embedded in a web page or installed as an add-on. The agent is optionally provided by Client Qualifier 1160. In various embodiments, the agent can find out processing power of Client 1110A, decoding and display capabilities of Client 1110A, lag time reliability and bandwidth of communication channels between Client 1110A and Video Server System 1120, a display type of Client 1110A, firewalls present on Client 1110A, hardware of Client 1110A, software executing on Client 1110A, registry entries within Client 1110A, and/or the like.

Client Qualifier 1160 includes hardware, firmware, and/or software stored on a computer readable medium. Client Qualifier 1160 is optionally disposed on a computing device separate from one or more other elements of Video Server System 1120. For example, in some embodiments, Client Qualifier 1160 is configured to determine the characteristics of communication channels between Clients 1110 and more than one instance of Video Server System 1120. In these embodiments the information discovered by Client Qualifier can be used to determine which instance of Video Server System 1120 is best suited for delivery of streaming video to one of Clients 1110.

Embodiments may be practiced with various computer system configurations including hand-held devices, microprocessor systems, microprocessor-based or programmable consumer electronics, minicomputers, mainframe computers and the like. The embodiments can also be practiced in distributed computing environments where tasks are performed by remote processing devices that are linked through a network.

With the above embodiments in mind, it should be understood that the embodiments can employ various computer-implemented operations involving data stored in computer systems. These operations are those requiring physical manipulation of physical quantities. Any of the operations described herein that form part of the embodiments are useful machine operations. The embodiments also relate to a device or an apparatus for performing these operations. The apparatus may be specially constructed for the required purpose, such as a special purpose computer. When defined as a special purpose computer, the computer can also perform other processing, program execution or routines that are not part of the special purpose, while still being capable of operating for the special purpose. Alternatively, the operations may be processed by a general purpose computer selectively activated or configured by one or more computer programs stored in the computer memory, cache, or obtained over a network. When data is obtained over a network the data may be processed by other computers on the network, e.g., a cloud of computing resources.

One or more embodiments can also be fabricated as computer readable code on a computer readable medium. The computer readable medium is any data storage device that can store data, which can be thereafter be read by a computer system. Examples of the computer readable medium include hard drives, network attached storage (NAS), read-only memory, random-access memory, CD-ROMs, CD-Rs, CD-RWs, magnetic tapes and other optical and non-optical data storage devices. The computer readable medium can include computer readable tangible medium distributed over a network-coupled computer system so that the computer readable code is stored and executed in a distributed fashion.

Although the method operations were described in a specific order, it should be understood that other housekeeping operations may be performed in between operations, or operations may be adjusted so that they occur at slightly different times, or may be distributed in a system which allows the occurrence of the processing operations at various intervals associated with the processing, as long as the processing of the overlay operations are performed in the desired way.

Although the foregoing embodiments have been described in some detail for purposes of clarity of understanding, it will be apparent that certain changes and modifications can be practiced within the scope of the appended claims. Accordingly, the present embodiments are to be considered as illustrative and not restrictive, and the embodiments are not to be limited to the details given herein, but may be modified within the scope and equivalents of the appended claims.

What is claimed is:

1. A head-mounted display (HMD) comprising:
a screen;
a processor;
a gaze tracking module for tracking eye movement;
a motion tracker module in communication with the processor, the motion tracker module configured to track a motion of the HMD and to predict movement of the HMD based on tracked motion of the HMD and tracked eye movement;
a display buffer configured for receiving display data corresponding to views of a virtual reality world as determined by positions and orientations of the HMD, wherein the display data is received from a computing device remote from the HMD and includes rendered views of the virtual reality world; and
a display adjuster in communication with the processor, the display adjuster configured to produce adjusted display data to be stored in the display buffer that includes a portion of a previous frame as reprojection image data for reuse in a next frame, wherein the adjusted display data is generated by modifying the rendered views of the virtual reality world to compensate for predicted movement of the HMD;
wherein the reprojection image data corresponds to an overlap region that is included within a new view of the virtual reality world as presented by the next frame and a previous view of the virtual reality world as presented by the previous frame, wherein the reprojection image data is identified in part based on the predicted movement of the HMD;
wherein the adjusted display data is scanned to the screen.

2. The HMD of claim 1, further comprising:
a communications module operable to receive the display data including the rendered views of the virtual reality world from the computing device.

3. The HMD of claim 1, further comprising:
a memory configured for storing one or more video frames previously presented on the display.

4. The HMD of claim 1, wherein the display adjuster is configured to generate the reprojection image data and reuse it in response to movement of the HMD moving from the previous view of the virtual reality world to the new view of the virtual reality world.

5. The HMD of claim 1, wherein the reprojection image data of the next frame is displayed in a region of the screen corresponding to the overlap region of the new view.

6. The HMD of claim 1, wherein the motion tracker module tracks the motion of the HMD using inertial sensors, wherein the inertial sensors include one or more of an accelerometer, or magnetometer, or a gyroscope.

7. The HMD of claim 1, wherein the screen is one of a virtual retinal display (VRD), or a light-emitting diode display (LED), or an electroluminescent display (ELD), or electronic paper, or o a plasma display panel (PDP), or a liquid crystal display (LCD), or an organic light-emitting diode display (OLED), or a cathode ray tube display (CRT).

8. A method comprising:
tracking eye movement of a user;
tracking motion of a head-mounted display (HMD) at the HMD;
predicting movement of the HMD based on tracked motion of the HMD and tracked eye movement;
receiving, at a display buffer of the HMD, display data corresponding to views of a virtual reality world as determined by positions and orientation of the HMD for presentation on a screen, wherein the display data is received from a computing device remote from the HMD and includes rendered views of the virtual reality world;
producing adjusted display data to be stored in the display buffer that includes a portion of a previous frame as reprojection image data for reuse in a next frame, wherein the adjusted display data is generated by modifying the rendered views of the virtual reality world to compensate for predicted movement of the HMD,
wherein the reprojection image data corresponds to an overlap region that is included within a new view of the virtual reality world as presented by the next frame and a previous view of the virtual reality world as presented by the previous frame, wherein the reprojection image data is identified in part based on the predicted movement of the HMD; and
scanning the adjusted display data including the reprojection image data to the screen.

9. The method of claim 8, further comprising:
receiving at a communications module of the HMD the display data including the rendered views of the virtual reality world from the computing device.

10. The method of claim 8, further comprising:
storing one or more video frames previously presented on the display in memory.

11. The method of claim 8, further comprising:
reusing the reprojection data in response to movement of the HMD moving from the previous view of the virtual reality world to the new view of the virtual reality world.

12. The method of claim 8, further comprising:
displaying the reprojection image data of the next frame in a region of the screen corresponding to the overlap region of the new view.

13. The method of claim 8, wherein the tracking motion of the HMD is performed using inertial sensors, wherein the inertial sensors include one or more of an accelerometer, or magnetometer, or a gyroscope.

14. The method of claim 8, wherein the screen is one of a virtual retinal display (VRD), or a light-emitting diode display (LED), or an electroluminescent display (ELD), or electronic paper, or o a plasma display panel (PDP), or a liquid crystal display (LCD), or an organic light-emitting diode display (OLED), or a cathode ray tube display (CRT).

15. A non-transitory computer-readable storage medium storing a computer program, the computer-readable storage medium comprising:
program instructions for tracking eye movement of a user;
program instructions for tracking motion of a head-mounted display (HMD) at the HMD;
program instructions for predicting movement of the HMD based on tracked motion of the HMD and tracked eye movement;
program instructions for receiving, at a display buffer of the HMD, display data corresponding to views of a virtual reality world as determined by positions and orientation of the HMD for presentation on a screen, wherein the display data is received from a computing device remote from the HMD and includes rendered views of the virtual reality world;
program instructions for producing adjusted display data to be stored in the display buffer that includes a portion of a previous frame as reprojection image data for reuse in a next frame, wherein the adjusted display data is generated by modifying the rendered views of the virtual reality world to compensate for predicted movement of the HMD,
wherein the reprojection image data corresponds to an overlap region that is included within a new view of the virtual reality world as presented by the next frame and a previous view of the virtual reality world as presented by the previous frame, wherein the reprojection image data is identified in part based on the predicted movement of the HMD; and
program instructions for scanning the adjusted display data including the reprojection image data to the screen.

16. The computer-readable storage medium of claim 15, further comprising:
program instructions for receiving at a communications module of the HMD the display data including the rendered views of the virtual reality world from the computing device.

17. The computer-readable storage medium of claim 15, further comprising:
program instructions for storing one or more video frames previously presented on the display in memory.

18. The computer-readable storage medium of claim 15, further comprising:
program instructions for reusing the reprojection data in response to movement of the HMD moving from the previous view of the virtual reality world to the new view of the virtual reality world.

19. The computer-readable storage medium of claim 15, further comprising:
program instructions for displaying the reprojection image data of the next frame in a region of the screen corresponding to the overlap region of the new view.

20. The computer-readable storage medium of claim 15, wherein the tracking motion of the HMD is performed using inertial sensors, wherein the inertial sensors include one or more of an accelerometer, or magnetometer, or a gyroscope.

* * * * *